United States Patent [19]

Pezeshki et al.

[11] Patent Number: 5,291,502
[45] Date of Patent: Mar. 1, 1994

[54] ELECTROSTATICALLY TUNABLE OPTICAL DEVICE AND OPTICAL INTERCONNECT FOR PROCESSORS

[75] Inventors: Bardia Pezeshki, Huntington Beach; James S. Harris, Jr., Stanford, both of Calif.

[73] Assignee: The Board of Trustees of the Leland Stanford, Jr. University, Stanford, Calif.

[21] Appl. No.: 939,903

[22] Filed: Sep. 4, 1992

[51] Int. Cl.$^5$ .................................. H01S 3/10
[52] U.S. Cl. ........................ 372/20; 372/96; 372/92; 372/98; 372/107; 372/108
[58] Field of Search ............... 372/20, 92, 98, 99, 372/107, 108, 96

[56] References Cited

U.S. PATENT DOCUMENTS 4,596,050  6/1986  Rogers .................. 455/607
5,052,016  9/1991  Mohbobzadeh et al. ........ 372/96
5,202,897  4/1993  Whithead ................. 372/93

OTHER PUBLICATIONS

Larry J. Hornbeck, "128×128 Deformable Mirror Device", IEEE Trans. Electron. Devices, vol. ED-30, No. 5, May 1983, pp. 539-545.

Mallinson, S. R., et al., "Miniature Micromachined Fabry-Perot Interferometers in Silicon", Electronics Letters, 24th Sep. 1987, vol. 23, No. 20, pp. 1041-1043.

R. Mark Boysel, "A 128×128 frame-addressed deformable mirror spatial light modulator", Optical Engineering, Sep. 1991, vol. 30, No. 9, pp. 1422-1427.

Jewell, J. L., et al., "Microlasers", Scientific American, Nov. 1991, pp. 86-94.

Photonics Research Incorporated brochure entitled "Microlaser Arrays" (including papers), Jun. 1992.

*Primary Examiner*—Léon Scott, Jr.
*Attorney, Agent, or Firm*—Flehr, Hohbach, Test, Albritton & Herbert

[57] ABSTRACT

A microlaser is described which is electrostatically tunable. One of the reflectors includes at least one reflecting part whose distance from the other reflector can be adjusted to change the effective optical distance between the reflectors and thus tune the optical frequency at which lasing occurs. The disclosure brings out that the inventive aspect is also applicable to other optical devices having reflectors defining a Fabry-Perot cavity. An optical interconnecting scheme for processors using the microlaser is also described.

17 Claims, 5 Drawing Sheets

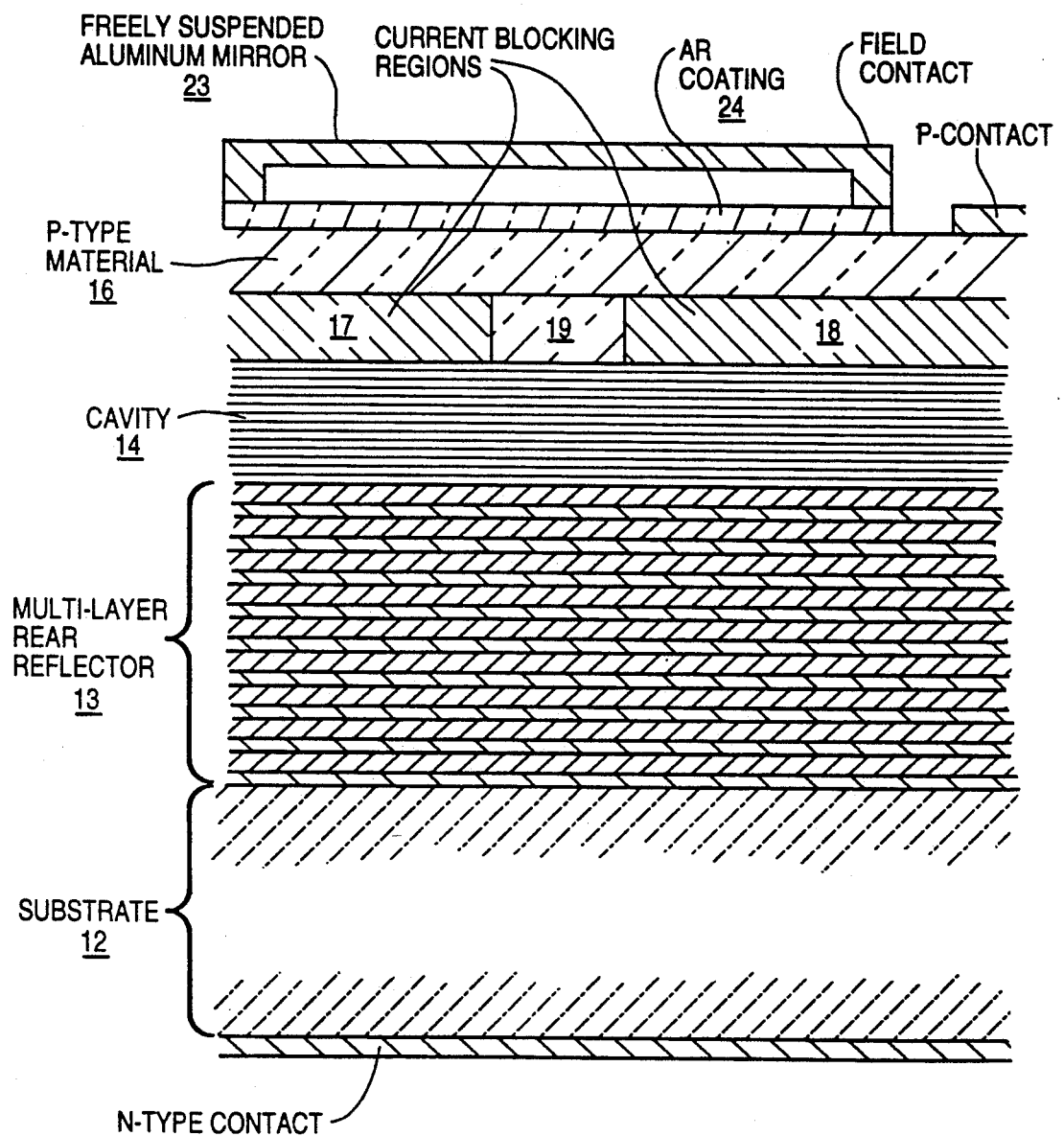
FIG_1

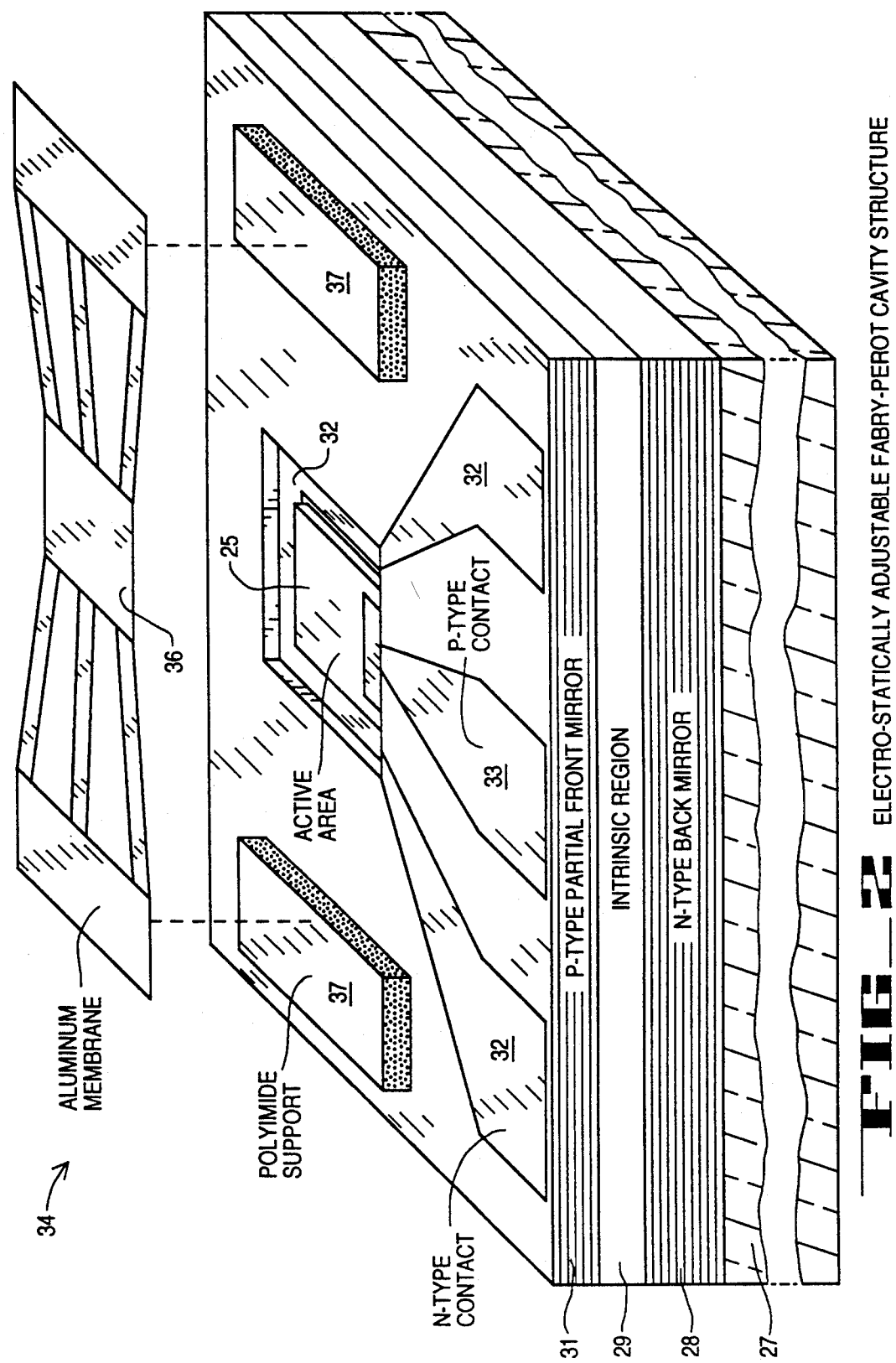
FIG_2  ELECTRO-STATICALLY ADJUSTABLE FABRY-PEROT CAVITY STRUCTURE

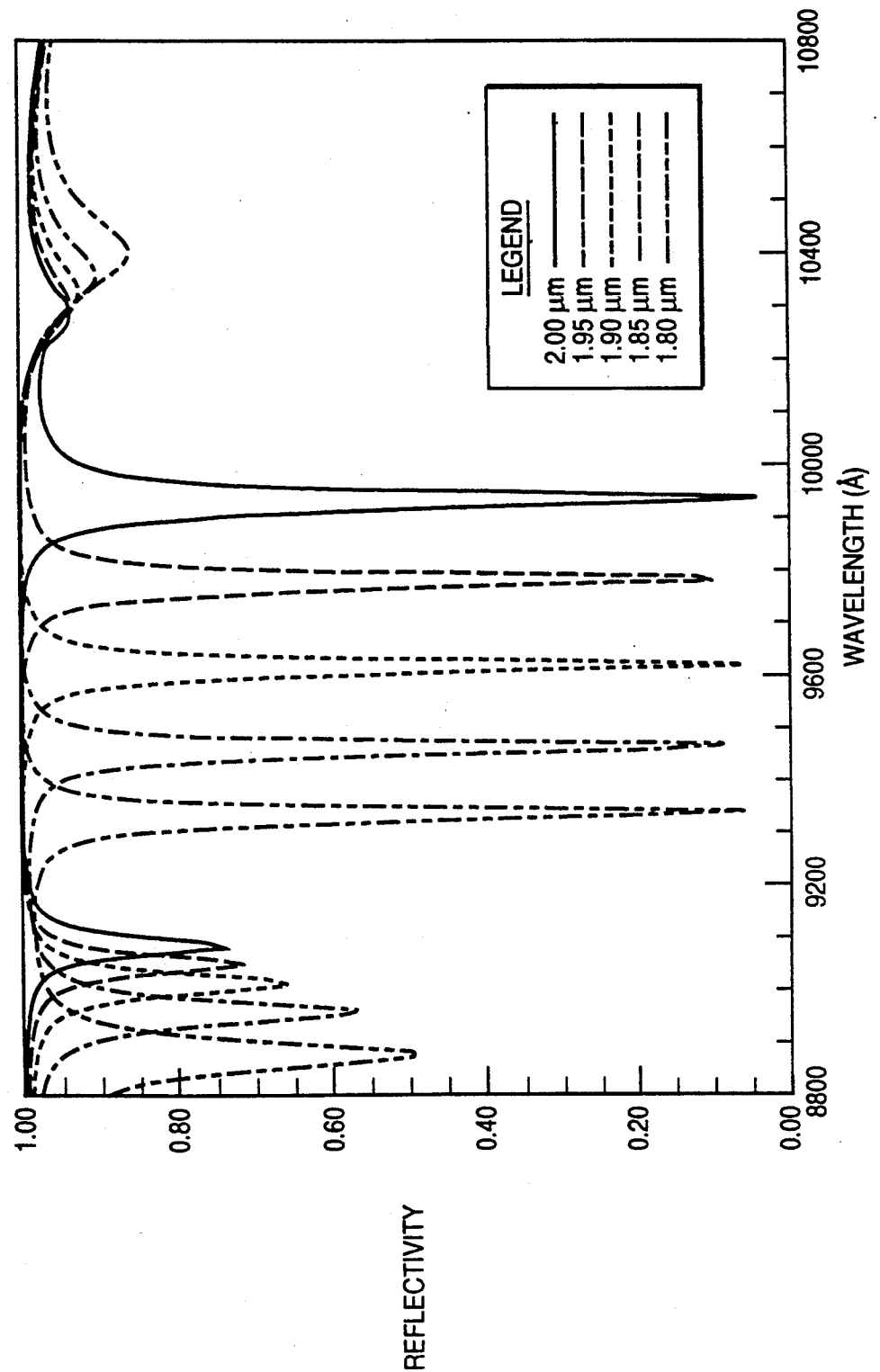

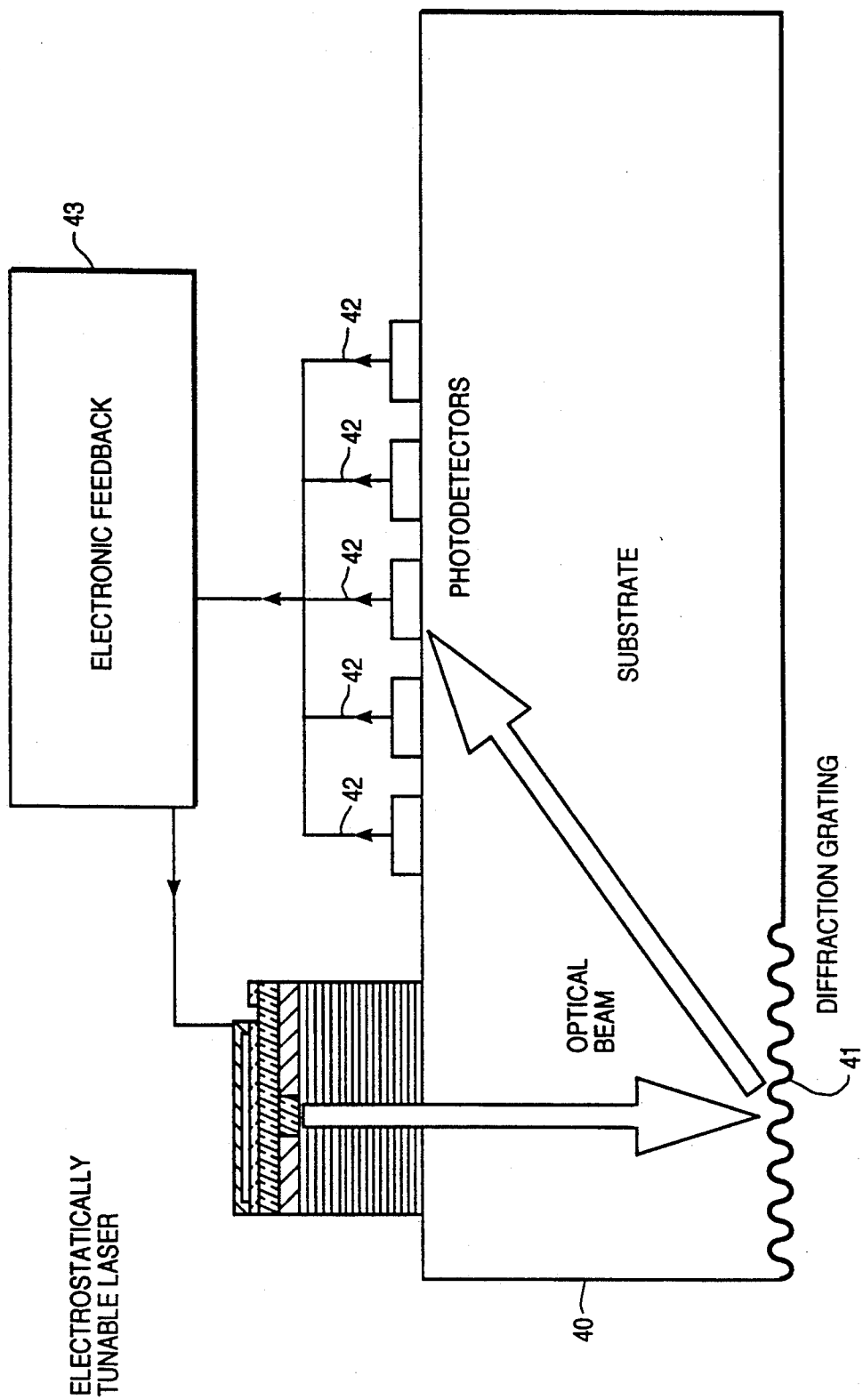
FIG_4

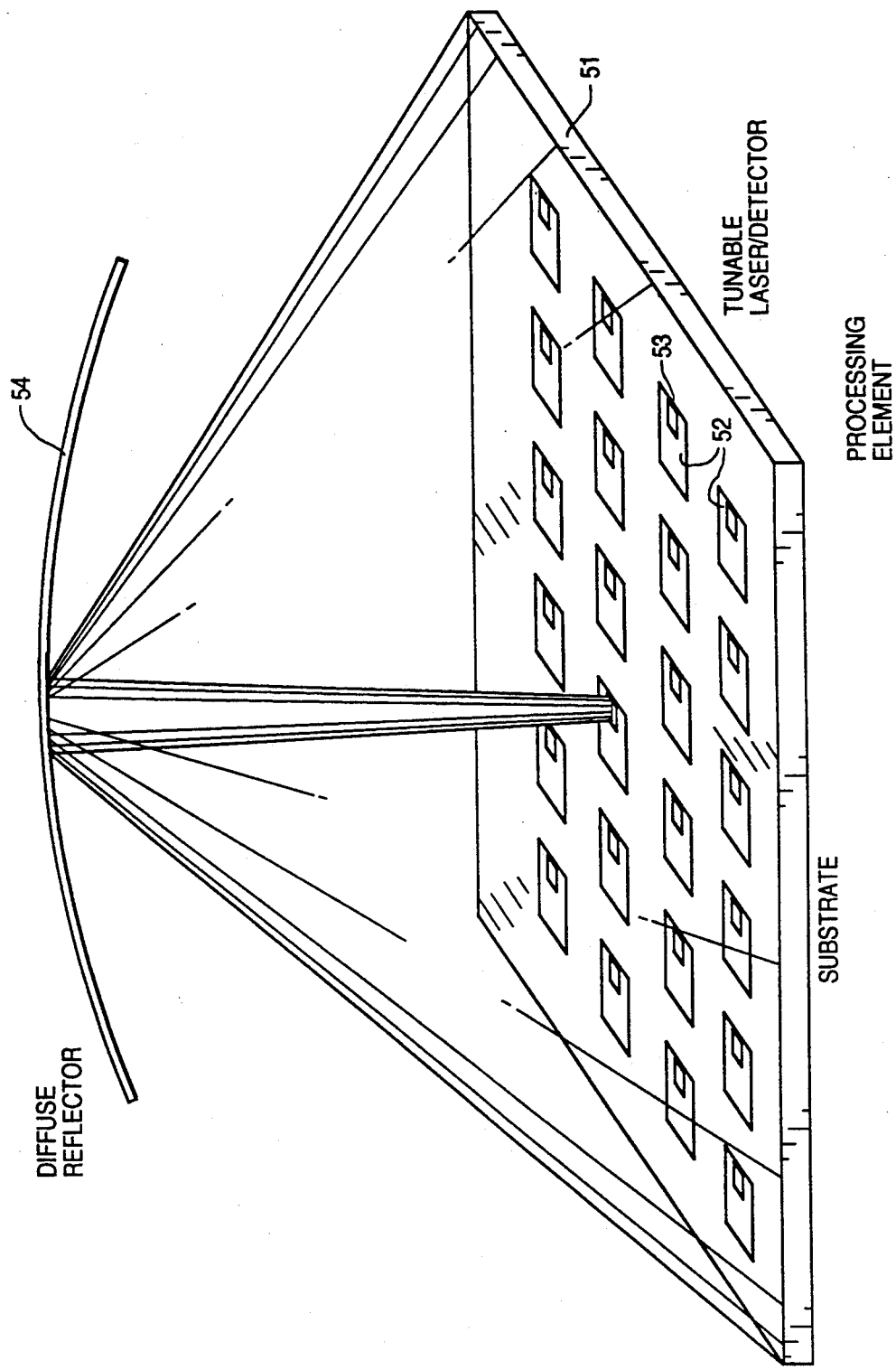

ELECTROSTATICALLY TUNABLE OPTICAL DEVICE AND OPTICAL INTERCONNECT FOR PROCESSORS

BACKGROUND OF THE INVENTION

The present invention relates to optical devices and, more particularly, to a tunable microlaser and other monolithically integrated Fabry-Perot cavity optical devices, as well as an optical interconnect for processors.

The advent of microlasers (sometimes referred to in the art as vertical-cavity surface emitting lasers) has been met with much excitement. A microlaser is many orders of magnitude smaller than a conventional diode laser. This miniaturization of the lasing phenomena is important in its own right, as well as providing other advantages. Moreover, microlasers and other Fabry-Perot cavity devices are fabricated by relatively well known techniques, the same techniques used to fabricate integrated circuitry. The article entitled "Microlasers" appearing on page 86 et seq. of the November 1991 issue of *Scientific American* provides a good overview of microlasers and such article is incorporated herein by reference.

One difficulty with microlasers is that they are relatively inflexible. That is, they typically emit only one optical frequency of optical radiation. (The term "optical radiation", as used herein, means electromagnetic radiation in the visible wavelength spectrum and in other adjacent wavelength spectrums—typically radiation having a wavelength in the range of between 10 and 15,000 nm.) In this connection, a microlaser is a type of semiconductor laser. Many semiconductors exhibit optical gain when adequate electrical or optical stimulation is provided. This gain region can be quite broad in energy or wavelength, and displays a maximum that depends on the strength of the external stimulation and the nature of the semiconductor. A conventional waveguide semiconductor laser consists of a relatively long Fabry-Perot cavity with mirrors spaced on the order of 200 $\mu$m apart. For such a long cavity, the Fabry-Perot resonances are closely spaced in wavelength, and, in the simplest case, the lasing wavelength of the device occurs at the resonance wavelength with the maximum gain. Such a device can be tuned to different wavelengths by adjusting the temperature of the semiconductor, since the maximum gain shifts in wavelength as the temperature changes. This method has a very limited tuning range, and the tuning time is on the order of seconds.

An alternative method of tuning conventional semiconductor lasers is to fabricate distributed mirrors at the ends of the waveguide. These mirrors are only reflective at a narrow range of wavelengths that depends on the spacings in the distributed mirror. Lasing occurs at the Fabry-Perot mode where the reflectivity is highest in the mirrors. The effective spacing (effective optical distance) between the mirrors and therefore the lasing wavelength can be changed in such a structure by modulating the refractive index in the distributed mirror regions. This can be accomplished by non-linear optical effects, such as carrier induced index modulation. Generally, such methods cause heating and parasitic frequency changes. Since non-linear optical effects tend to be very weak, and they limit the tuning range of such devices to less than about 10 nm in wavelength.

In contrast to the above, the Fabry-Perot cavity of a microlaser is very short, on the order of a few wavelengths, and thus the mirrors of such a laser are made to have much higher reflectivities to compensate for the lower total gain. Microlasers are fabricated on a substrate by either being grown epitaxially or by deposition, and the mirrors consist of quarter-wave periods of semiconductor for the bottom mirror, and some combination of quarter-wave semiconductor or dielectric layers as the top reflector. Since the cavity is very short, the Fabry-Perot modes are spaced far apart, and to get any lasing at all, at least one Fabry-Perot mode must be in the gain region of the semiconductor in the cavity.

SUMMARY OF THE INVENTION

The present invention is a microlaser or other optical device having a monolithically integrated Fabry-Perot cavity which is tunable electrostatically in a quite simple manner. The invention also includes an optical interconnect arrangement for a processor based on such a microlaser.

In its most basic aspects, the microlaser is one in which the effective optical distance between the reflectors is adjustable to tune the optical frequency to which the Fabry-Perot cavity responds. (In a microlaser this response is lasing.) Most desirably, this effective optical distance between reflectors is adjusted by creating a potential difference electrostatically between one of the reflectors and at least a portion of the other.

A preferred embodiment of the microlaser of the invention includes a vertical cavity Fabry-Perot structure with a quarter-wave semiconductor bottom reflector or, in other words, mirror. In keeping with the invention, part of the top mirror is mechanically movable using electrostatic force. A monolithically fabricated aluminum membrane which is part of the top mirror is deflectable by applying a voltage between the membrane and the remainder of the device. The changed spacing between the aluminum and the remainder of the device causes the Fabry-Perot resonance to shift and alter the resonance wavelength of the cavity.

The inventive aspects of the microlaser also can be incorporated in other monolithic integrated type optical devices having Fabry-Perot cavities, such as detectors.

The invention further includes an optical interconnect for a processor, based on an array of interconnecting elements which are microlasers and detectors. The array of microlasers and detectors enables parallel linking of processing elements. Such communication structure includes not only such an array, but also a diffuser or other directing means to direct optical radiation to at least two different ones of the interconnecting elements. Most desirably, for flexibility each of the interconnecting elements is frequency tunable. Also, each either includes both a microlaser and a detector of optical radiation or each is designed to provide both lasing functions and detection functions sequentially.

Other features and advantages of the invention either will become apparent or will be described in connection with the following, more detailed description of preferred embodiments of the invention.

BRIEF DESCRIPTION OF THE DRAWING

With reference to the accompanying drawing:

FIG. 1 is a schematic view illustrating principles of the invention, such view being an enlarged sectional view of a microlaser construction incorporating the invention;

FIG. 2 is an embodiment of the invention;

FIG. 3 is a graph showing how the reflectivity spectra of a monolithically integrated optical device incorporating the invention changes as the effective optical distance between the mirrors of a Fabry-Perot cavity of such device is changed;

FIG. 4 is a schematic view of an implementation of a microlaser incorporating the invention, such implementation using an integrated diffraction grating to provide electronic feedback for frequency stabilization; and FIG. 5 is an illustration of an optical communication structure of the invention for a processor.

DETAILED DESCRIPTION OF PREFERRED EMBODIMENTS

The following relatively detailed description is provided to satisfy the patent statutes. However, it will be appreciated by those skilled in the art that various changes and modifications can be made without departing from the invention.

FIG. 1 is a schematic view illustrating principles of the invention. Such principles are explained via a microlaser or, in other words, a vertical cavity surface emitting laser.

The microlaser, generally referred to by the reference numeral 11, includes a substrate 12 upon which the remainder of the same is formed. It has a complete rear reflector 13 of a stack of alternating quarter-wave layers of two different materials, and the device has a Fabry-Perot cavity region 14 that contains the active material. For simplicity of manufacture the substrate most desirably is a semiconductive gallium arsenide wafer and the two different materials making up the quarter-wave layers then may be aluminum gallium arsenide (AlGaAs), and aluminum arsenide (AlAs). The cavity region of this microlaser may be composed of indium gallium arsenide quantum wells with gallium arsenide barriers. It will be recognized, however, that other materials and combinations can be used without departing from the spirit of the invention.

Part 16 of the top reflector is made up of p-type gallium arsenide, and a pair of current blocking regions 17 and 18 are formed by a deep proton implant to assure appropriate containment of the lasing action as is conventional. An active region 19 for the lasing action is thereby defined.

In keeping with the invention, the upper reflector differs from a conventional surface-emitting laser structure in that it includes a freely suspended mirror layer 23 of a conductive material, such as aluminum. It (the microlaser), the mirror 23 and the remainder of the device can be formed by conventional epitaxial growth techniques, such as molecular beam epitaxy (MBE) or chemical vapor deposition (CVD). The relative position of layer 23 to the rest of the structure is changeable by the application of an electrostatic field. The result of this is that the effective optical distance between the two reflectors making up the cavity is adjustable. That is, the average position of the constituents of the second reflector relative to the cavity changes, with a change in the position of layer 23. Since the resonance wavelength depends on this position, the characteristic wavelength of the microlaser is continually tuned by varying the applied voltage and thereby the electrostatic field between the layer 23 and the remainder of the device. Thus, the electrostatic field can be construed as means for changing the effective optical distance between the laser reflectors. Electrical contact with the aluminum layer 23 is at its top surface, although it could be made to its bottom surface. Electrical isolation of layer 23 from the remainder of the device is achieved in a manner similar to conventional structures and is well within the skill of the art.

It is necessary to provide energy within the microlaser to achieve lasing action. For example, in FIG. 1 the device electrically is a p-i-n junction, with the n-contact being made through the substrate to an ntype bottom mirror, while the top contact is made to the p-doped top layer.

Various optical coatings can be used on the wafer surface to adjust the relative importance of the deformable layer on influencing the Fabry-Perot mode. The highest sensitivity to the layer or, in other words, membrane 23 position is achieved by eliminating all reflections from the wafer surface using an anti-reflection (AR) coating layer 24. Where high reflectivities are required, a partial mirror can be fabricated on the wafer surface. This would yield a higher effective front mirror reflectivity but reduce the effect of the movable layer.

As mentioned earlier, the movable layer can be fabricated using established methods. For example, photosensitive polyimide can be applied to the entire wafer, and the material exposed but not developed. Aluminum then may be sputtered on the wafer and patterned using standard techniques. The polyimide is then developed to form the air gap region between the aluminum and the wafer while leaving polyimide supports.

It should be noted that it is not new to electrostatically control optical elements in optical devices. An example includes the torsional metal mirrors formed lithographically using a sacrificial layer of material, leading to a structure that is freely suspended above a wafer. Conducting layers are placed on the suspended layer and on the semiconductor and a DC electrostatic field is applied therebetween. The field deforms the layer and mechanically moves the layer. No such arrangement is known or is suggested for changing the optical distance between mirrors in a Fabry-Perot cavity optical device, much less in a microlaser. The only known current application of this approach is to deflect optical beams that impinge on the side of the deformable layer opposed to that used in this invention for tuning Fabry-Perot cavities. The technology in the past has also been limited to the well-studied silicon systems that are not used in the fabrication of microlasers or high performance detectors.

An embodiment of the microlaser of the invention is shown in FIG. 2. In this case a partial front mirror is used in addition to the movable membrane.

In basic terms, the microlaser 26 of FIG. 2 is formed by deformation of layers on a gallium arsenide (GaAs) substrate wafer represented at 27. It includes an active region at 25 which is isolated by a surface proton implant outside such active region or area. The rear reflector or mirror 28 is a stack of alternating layers of material as in the schematic representation discussed above. The lasing cavity is formed as is conventional by an intrinsic region 29 and, as mentioned previously, a partial front mirror is formed by a stack 31 of alternating layers of differing materials.

Both the n-type contact and p-type contact are made to the front of the wafer, with an etched region around the active area used to contact the n-type layer. The n-type contact is represented at 32 whereas the p-type is represented at 33. These contacts are simply formed from a layer of an electrically conductive material, such as gold.

In accordance with the invention, a movable layer or membrane 34 is included as part of the front mirror. The central region 36 is solid so as to stay flat and perpendicular to the wafer, and deformation in accordance with the invention occurs in the connecting stripes.

Polyimide supports 37 are used to maintain the membrane above the wafer surface. The same effect as that obtained from the shape of the layer 34 can be achieved by making the central region 36 directly above the active region 25 thicker than the supporting stripes. A slight curvature in the membrane might also be beneficial, reducing the diffraction loss in the cavity and lowering the laser threshold. Various optical coatings can be placed above or below the membrane to enhance the optical reflectivity, while the composition can be adjusted to maximize elasticity, while maintaining reliability.

Supports for the membrane other than the use of polyimide pillars 37 can also be used. For example, supports or posts can be formed from $SiO_2$ or metals. If the membrane is not partially transparent, the light can be coupled out and/or in the cavity through a transparent substrate (such as 1 $\mu$m radiation for a GaAs substrate), or by removing the substrate entirely after the microlaser is made, using an etch or lift off technique. (If the substrate is removed, it should be noted that it was part of the microlaser and optical device combination at one time.)

When the p-n junction is strongly forward biased, the resulting population inversion will lead to gain, and the microlaser of the invention will emit light corresponding to the wavelength of the cavity resonance. If this resonance is tuned by electrostatically moving the freely suspended membrane, the emission wavelength will change.

It should be noted that the embodiment of FIG. 2 may be operated as a tunable detector. If the p-n junction is reverse biased, photocurrent is generated by receipt in the cavity of optical radiation. The peak sensitivity of the detector occurs at the cavity resonance, and this can be detected by moving the freely suspended membrane. If the detected optical frequency is only one of the optical frequencies being received by the cavity, the detector acts, in effect, as a "filter" to select the desired optical frequency.

FIG. 3 is a graph illustrating the efficacy of the instant invention. It is based on the simulation of an optical device designed to be a tunable detector, with a tuning range between 900 nm and 1 $\mu$m. The device is simulated to be fabricated on a n-type GaAs substrate using an epitaxial growth technique. The rear mirror is simulated to consist of 10.5 periods of 678 Å GaAs layers with 792 Å AlAs layers, with AlAs layers on the outsides of the stack. This combination gives a reflectivity of about 88% over a region from 880 nm to 1.01 $\mu$m. The mirror is doped n-type to render it conductive. The cavity is simulated to consist of 15×75 Å $In_{0.2}Ga_{0.8}As$ quantum wells with 150 Å GaAs barriers. Such quantum wells absorb light of the same wavelength range. However, a GaAs substrate would be transparent to this light, allowing coupling through the substrate. For the upper mirror, 2800 Å of p-doped GaAs would be grown to act as a conducting layer. The wafer would be processed as shown in FIG. 2, with an aluminum layer suspended 2 $\mu$m above the wafer using polyimide supports.

FIG. 3 shows the reflectivity of the device described above as the distance from the aluminum mirror to the wafer is modulated electrostatically. The distances in the figure refer to the spacing between the aluminum membrane and the wafer surface. In the simulation, substrate absorption is neglected and quantum well absorption is assumed constant. In accordance with the invention, the Fabry-Perot dip is seen to move from just under 1 $\mu$m to just above 930 nm as the spacing is changed from 1 $\mu$m to 1.85 $\mu$m. Since the photocurrent peak is at the position of the dip, the wavelength sensitivity of the device can be modulated with voltage. The dips at about 1.04 $\mu$m and 890–910 nm correspond to other Fabry-Perot modes.

For applications where the absolute wavelength needs to be accurately fixed, electronic feedback can be added either in a monolithic or in a hybrid way. That is, control means can be provided for maintaining a selected effective optical distance between the reflectors. FIG. 4 is a schematic of how electronic feedback can be used as such control means to stabilize the lasing wavelength using a diffraction grating on the backside of the wafer represented at 40. Part of the optical beam exits the electrostatically tunable microlaser from the rear reflector into the substrate as illustrated. The light is partially diffracted by a grating 41 etched on the backside of the wafer and is detected by a series of photodetectors 42 on the front side of the wafer. Since the angular diffraction depends on the wavelength, the response from the photodetectors can be used to stabilize the wavelength. That is, electronic feedback means for reacting to the output of the photodetectors 42 by adjusting the voltage applied to the movable membrane of the cavity is represented at 43. In this way, the effective optical distance of the cavity is changed to tune the optical cavity to the desired optical frequency. The details of providing such a feedback arrangement are well within the skill in the art.

An application of the microlaser of the invention is providing optical links within a computer or other information processor. Currently optical interconnects for processors are point to point. For example, in electronic processors wires are sometimes replaced by optical fibers, to allow higher bandwidth or lower power consumption. Another approach is to use free space optical links, such as a Self-Electro-Optic-Device (SEED) array. With this method, arrays of optical devices are imaged and accurately focused on top of each other, aligning each device with another in a different array. Both the fiber and the free space approach are limited in that they provide fixed connections between devices and have little flexibility in switching these connections. Using arrays of tunable lasers and detectors with processing elements, on the other hand, allows connections between processing elements that can be switched by simply changing the wavelengths of individual links. For example, each processing element can transmit via its microlaser on a fixed wavelength, while other processing elements can connect or disconnect themselves by tuning their detector to this wavelength or to other wavelengths. The very large optical bandwidth can allow integration of many processing elements for parallel computing or neural network applications. For example in a 1000 Å tuning range about a wavelength of 1 $\mu$m, there can be over 20,000 channels communicating at 10 GHZ. FIG. 5 is an embodiment of this interconnection scheme. An array 51 of processing elements 52, each equipped with a tunable laser/detector 53, broadcasts to the entire array, using a diffuse reflector 54. The other processing elements in the array can communicate with the particular processing elements by tuning their detectors to this wavelength. The processing elements could be simple threshold switches of, for example, a neural network structure or could be complete microprocessors with memory and logic thereby forming a parallel computer. Each processing element can be equipped with either one tunable microlaser/detector or many such units for higher data rates. Moreover, a single optical device can be used to provide both the lasing function and a detection function by being sequentially clocked between the two modes of operation.

It should be noted that while from the very broad standpoint and in some instances the microlasers and detectors need not be tunable as long as differing optical frequencies are provided by the array, for increased flexibility it is highly desirable that the tuning function be included. The processing element can be an electrical one or another type, such as an optical one.

There are many other applications for a tunable microlaser and/or tunable detector or other Fabry-Perot cavity optical device. In wavelength division multiplexing (WDM) applications, where many optical communication channels are transmitted at different wavelengths on the same optical fiber or waveguide, a single device can be used to generate and detect the different channels. Other potential applications are in optical analysis and measurement. A tunable microlaser allows accurate spectrophotometry and absorption measurements in determining the composition and quality of materials.

As mentioned at the beginning of the detailed description, Applicant is not limited to the specific embodiment(s) described above. Various changes and modifications can be made. For example, different appropriate materials can be used, including for the supports and the membrane, and different modes of electrical contact and isolation can be used. The claims, their equivalents and their equivalent language define the scope of protection.

We claim:

1. A microlaser comprising:
a semiconductor substrate;
means formed on a surface of said substrate defining a first reflector for optical radiation;
means defining a Fabry-Perot lasing cavity for optical radiation, which lasing cavity is positioned to receive optical radiation reflected by said first reflector;
means defining a second reflector for optical radiation positioned to reflect optical radiation it receives from said lasing cavity through said lasing cavity toward said first reflector; and
means for adjusting the effective optical distance between said reflectors to tune the optical frequency at which lasing in said cavity occurs.

2. The microlaser of claim 1 wherein said first reflector is defined on said surface of said substrate by a stack of alternating layers of material.

3. The microlaser of claim 1 wherein said means for adjusting includes means for creating a potential difference between at least a portion of said second reflector and another element of said microlaser to control said effective optical distance between said reflectors.

4. The microlaser of claim 1 wherein said means defining a lasing cavity includes a semiconductive material as a lasing medium for optical radiation.

5. The microlaser of claim 4 wherein said semiconductive material is gallium arsenide.

6. The microlaser of claim 1 further including control means for maintaining a selected output frequency.

7. The microlaser of claim 6 wherein said control means includes a detector for detecting said output frequency, and feedback means for reacting to the output of said detector by adjusting said effective optical distance to tune said optical cavity to provide a desired optical frequency.

8. The microlaser of claim 1 wherein said first reflector is defined on said surface of said substrate by a stack of alternating layers of material, and said lasing medium is a layer of semiconductive material formed on a surface of said stack.

9. The microlaser of claim 8 wherein said means defining said second reflector includes in part a plurality of layers of material defining a reflective surface for optical radiation, and wherein said means for adjusting includes means for changing the distance of at least one of said layers defining said first reflector to correspondingly change said effective optical distance between said reflectors.

10. An optical interconnecting arrangement for processing elements comprising:
A. a semiconductive substrate having an array of optical interconnects thereon, each of which includes;
means formed on a surface of said substrate defining a first reflector for optical radiation;
means defining a Fabry-Perot cavity for optical radiation, positioned to receive optical radiation reflected by said first reflector;
means defining a second reflector for optical radiation positioned to reflect optical radiation it receives from said cavity toward said first reflector; and
B. means positioned to direct optical radiation to at least two optical interconnects of said array to provide communication therebetween.

11. The arrangement of claim 10 wherein the effective optical distance between the reflectors of at least one of said processing elements is adjustable to tune the optical frequency at which lasing in the cavity of said microlaser occurs.

12. The arrangement of claim 10 wherein said means positioned to direct optical radiation to at least two processing elements of said array does so by reflection of said optical radiation.

13. The arrangement of claim 10 wherein each of said optical interconnects further has a processing element associated therewith.

14. The arrangement of claim 13 wherein each of said processing elements includes at least a pair of Fabry-Perot cavities, one of which has a lasing medium therein.

15. The arrangement of claim 10 wherein said means defining a Fabry-Perot cavity includes means defining a lasing cavity for optical radiation; one of said reflectors transmits the portion of optical radiation received thereby to provide an output beam of optical radiation; and said means positioned to direct optical radiation to at least two processing elements of said array, is positioned to direct the output beam of optical radiation from one of said processing elements to the other.

16. An optical device comprising:
a semiconductive substrate;
means formed on a surface of said substrate defining a first reflector for optical radiation;
means defining a Fabry-Perot cavity for optical radiation, which cavity is positioned to receive optical radiation reflected by said first reflector and includes:
   means defining a second reflector for optical radiation spaced from said first reflector by an effective optical distance to reflect optical radiation towards said first reflector; and
   means for adjusting the effective optical distance between said reflectors to tune the optical frequency of said Fabry-Perot cavity.

17. The optical device of claim 16 wherein said device is a detector of optical frequencies, and means are provided for detecting the optical frequency of optical radiation resonated between said reflectors.

* * * * *